US007666981B1

(12) United States Patent
Chai et al.

(10) Patent No.: US 7,666,981 B1
(45) Date of Patent: Feb. 23, 2010

(54) INHIBITORS OF PROSTASIN

(75) Inventors: Karl X. Chai, Winter Springs, FL (US); Li-Mei Chen, Winter Springs, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 142 days.

(21) Appl. No.: 10/434,349

(22) Filed: May 8, 2003

Related U.S. Application Data

(60) Provisional application No. 60/379,469, filed on May 10, 2002.

(51) Int. Cl.
*C07K 14/00* (2006.01)
(52) U.S. Cl. .................. 530/324; 530/325; 530/326; 514/2; 514/12; 514/13; 514/14
(58) Field of Classification Search .............. 514/2, 514/12, 13, 14; 530/324, 325, 326, 350
See application file for complete search history.

(56) References Cited

U.S. PATENT DOCUMENTS

| | | | | |
|---|---|---|---|---|
| 5,326,562 | A * | 7/1994 | Scott ................. | 424/94.64 |
| 5,686,419 | A | 11/1997 | Powers et al. ............ | 514/18 |
| 5,871,917 | A | 2/1999 | Duffy ..................... | 435/6 |
| 6,043,033 | A | 3/2000 | Bandman et al. .......... | 435/6 |
| 6,048,970 | A | 4/2000 | Lal et al. ............... | 536/23.5 |
| 6,075,136 | A | 6/2000 | Tang et al. ............. | 536/23.1 |
| 6,090,559 | A | 7/2000 | Russell et al. ............ | 435/6 |
| 6,090,786 | A | 7/2000 | Augustyns et al. ........ | 514/19 |
| 6,107,049 | A | 8/2000 | Allard et al. ............ | 435/7.1 |
| 6,303,318 | B1 | 10/2001 | O'Brien .................. | 435/7.1 |
| 6,420,157 | B1 | 7/2002 | Darrow et al. ........... | 435/226 |
| 2001/0016331 | A1 | 8/2001 | Kominami et al. ........ | 435/7.95 |

FOREIGN PATENT DOCUMENTS

EP 000251505 * 1/1988

OTHER PUBLICATIONS

Chen (Int J Cancer 97(3), 323-329, 2002).*
Chen (The Prostate 66(9), 911-20, 2006).*
Donaldson (J. Biol. Chem. 277, 8338-8345, 2002).*
Aihara M. Lebovitz RM. Wheeler TM. Kinner BM. Ohori M. Scardino PT. Prostate specific antigen and gleason grade: an immunohistochemical study of prostate cancer. Journal of Urology. 151(6):1558-64, 1994.
Akazaki K. Stemmerman GN. Comparative study of latent carcinoma of the prostate among Japanese in Japan and Hawaii. Journal of the National Cancer Institute. 50(5):1137-44, 1973.
Bastacky SI. Wonjo KJ. Walsh PC. Carmichael MJ. Epstein JI. Pathological features of hereditary prostate cancer. Journal of Urology. 153(3 Pt 2):987-92, 1995.
Berteau P. Laribi A. Eschwege P. Lebars I. Dumars F. Benoit G. Loric S. Prostasin mRNA to detect prostate cells in blood of cancer patients. Clinical and Chemical Laboratory Medicine 37 (SS): S119, 1999.

Bussemakers MJ. van Moorselaar RJ. Giroldi LA. Ichikawa T. Isaacs JT. Takeichi M. Debruyne FM. Schalken JA. Decreased expression of E-cadherin in the progression of rat prostatic cancer. Cancer Research. 52(10):2916-22, 1992.
Carter H. Coffey D. Prostate Cancer: the magnitude of the problem in the United States. In *A Multidisciplinary Analysis of Controversies in the Management of Prostate Cancer*. (Eds. Coffey D. Resnick M. Door R. et al.), pp. 1-9, Plenum Press, 1988.
Carter HB. Piantadosi S. Isaacs JT. Clinical evidence for and implications of the multistep development of prostate cancer. Journal of Urology. 143(4):742-6, 1990.
Catalona WJ. Partin AW. Slawin KM. Brawer MK. Flanigan RC. Patel A. Richie JP. deKernion JB. Walsh PC. Scardino PT. Lange PH. Subong EN. Parson RE. Gasior GH. Loveland KG. Southwick PC. Use of the percentage of free prostate-specific antigen to enhance differentiation of prostate cancer from benign prostatic disease: a prospective multicenter clinical trial [see comments]. JAMA. 279(19):1542-7, 1998.
Denis LJ. Staging and prognosis of prostate cancer. European Urology. 24 Suppl 2:13-8, 1993.
Dong JT. Lamb PW. Rinker-Schaeffer CW. Vukanovic J. Ichikawa T. Isaacs JT. Barrett JC. KAI1, a metastasis.
Dong JT. Suzuki H. Pin SS. Bova GS. Schalken JA. Isaacs WB. Barrett JC. Isaacs JT. Down-regulation of the KAI1 metastasis suppressor gene during the progression of human prostatic cancer infrequently involves gene mutation or allelic loss. Cancer Research. 56(19):4387-90, 1996.
Dunn JE. Cancer epidemiology in populations of the United States—with emphasis on Hawaii and California—and Japan. Cancer Research. 35(11 Pt. 2):3240-5, 1975.
Emmert-Buck, et al., Laser Capture Microdissection *Science*, vol. 274, Nov. 8, 1997, pp. 998-1001.
Ernster VL. Barclay J. Increases in ductal carcinoma in situ (DCIS) of the breast in relation to mammography: a dilemma. [Review] [34 refs] Journal of the National Cancer Institute. Monographs. (22):151-6, 1997.
Fornaro M. Tallini G. Bofetiado CJ. Bosari S. Languino LR. Down-regulation of beta 1C integrin, an inhibitor of cell proliferation, in prostate carcinoma. American Journal of Pathology. 149(3):765-73, 1996.
Fornaro M. Manzotti M. Tallini G. Slear AE. Bosari S. Ruoslahti E. Languino LR. Beta1C integrin in epithelial cells correlates with a nonproliferative phenotype: forced expression of beta1C inhibits prostate epithelial cell proliferation. American Journal of Pathology, 153(4):1079-87, 1998.
Fornaro M. Tallini G. Zheng DQ. Flanagan WM. Manzotti M. Languino LR. p27(kip1) acts as a downstream effector of and is coexpressed with the beta1C integrin in prostatic adenocarcinoma. Journal of Clinical Investigation 103(3):321-9, 1999.

(Continued)

*Primary Examiner*—David Lukton
(74) *Attorney, Agent, or Firm*—Allen, Dyer, Doppelt, Milbrath & Gilchrist, P.A.

(57) ABSTRACT

A class of proteins useful as inhibitors of prostasin and method for identifying them are provided. These proteins have the structure wherein the amino acids P1-P4 from the scissile bond are respectively leu-ile-ala-arg and the amino acids at positions P5-P15 are serpin sequences.

4 Claims, 7 Drawing Sheets

OTHER PUBLICATIONS

Gao AC. Lou W. Dong JT. Isaacs JT. CD44 is a metastasis suppressor gene for prostatic cancer located on human chromosome 11p13. Cancer Research. 57(5):846-9, 1997.

Gleason DF. Classification of prostatic carcinomas. Cancer Chemotherapy Reports—Part 1. 50(3):125-8, 1966.

Gleason DF. Mellinger GT. Prediction of prognosis for prostatic adenocarcinoma by combined histological grading and clinical staging. Journal of Urology. 111(1):58-64, 1974.

Goyal J, Smith KM, Cowan JM, Wazer DE, Lee SW, Band V. The role for NES1 serine protease as a novel tumor suppressor. Cancer Res 58:4782-4786, 1998.

Greene GF. Kitadai Y. Pettaway CA. von Eschenbach AC. Bucana CD. Fidler IJ. Correlation of metastasis-related gene expression with metastatic potential in human prostate carcinoma cells implanted in nude mice using an in situ messenger RNA hybridization technique. American Journal of Pathology. 150(5):1571-82, 1997.

Greenlee RT, Murray T, Bolden S, Wingo PA. Cancer statistics, 1999. Ca: a Cancer Journal for Clinicians 2000;50:7-33.

Haenszel W. Kurihara M. Studies of Japanese migrants. I. Mortality from cancer and other diseases among Japanese in the United States. Journal of the National Cancer Institute. 49(1):43-68, 1968.

Hakalahti L. Vihko P. Henttu P. Autio-Harmainen H. Sonini Y. Vihko R. Evaluation of PAP and PSA gene expression in prostatic hyperplasia and prostatic carcinoma using northern-blot analyses, in situ hybridization and immunohistochemical stainings with monoclonal and bispecific antibodies. International Journal of Cancer. 55(4):590-7, 1993.

Hooper JD. Nicol DL. Dickinson JL. Eyre HJ. Scarman AL. Normyle JF. Stuttgen MA. Douglas ML. Loveland KA. Sutherland GR. Antalis TM. Testisin, a new human serine proteinase expressed by premeiotic testicular germ cells and lost in testicular germ cell tumors. Cancer Research. 59(13):3199-205, 1999.

Hwang ES. Esserman LJ. Management of ductal carcinoma in situ. [Review] [91 refs] Surgical Clinics of North America. 79(5):1007-30, viii, 1999.

Isaacs JT. Molecular markers for prostate cancer metastasis. Developing diagnostic methods for predicting the aggressiveness of prostate cancer. [Review] [92 refs] American Journal of Pathology. 150(5):1511-21, 1997.

Isaacs JT. Bova GS. Prostate Cancer. In *The Genetic Basis of Human Cancer* (Eds. Vogelstein B and Kinzler KW), pp. 653-660, McGraw-Hill Health Professions Division, 1998.

Kennedy AR. Chemopreventive agents: protease inhibitors. Pharmacol Therapeut 78:167-209, 1998.

Knuutila S. Aalto Y. Autio K. Bjorkqvist AM. El-Rifai W. Hemmer S. Huhta T. Kettunen E. Kiuru-Kuhlefelt S. Larramendy ML. Lushnikova T. Monni O. Pere H. Tapper J. Tarkkanen M. Varis A. Wasenius VM. Wolf M. Zhu Y. DNA copy number losses in human neoplasms. [Review] [197 refs] American Journal of Pathology. 155(3):683-94, 1999.

Liu DF. Rabbani SA. Induction of urinary plasminogen activator by retinoic acid results in increased invasiveness of human prostate cancer cells PC-3. Prostate. 27(5):269-76, 1995.

Lou W. Krill D. Dhir R. Becich MJ. Dong JT. Frierson HF Jr. Isaacs JT. Gao AC. Methylation of the CD44 metastasis suppressor gene in human prostate cancer. Cancer Research. 59(10):2329-31, 1999.

Lou J. Lubaroff DM. Hendrix MJ. Suppression of prostate cancer invasive potential and matrix metalloproteinase activity by E-cadherin transfection. Cancer Research. 59(15):3552-6, 1999.

Mignatti P. Rifkin DB. Biology and biochemistry of proteinases in tumor invasion. [Review] [306 refs] Physiological Reviews. 73(1):161-95, 1993.

Mirchandani D. Zheng J. Miller GJ. Ghosh AK. Shibata DK. Cote RJ. Roy-Burman P. Heterogeneity in intratumor distribution of p53 mutations in human prostate cancer. American Journal of Pathology. 147(1):92-101, 1995.

Nelson PS. Gan L. Ferguson C. Moss P. Gelinas R. Hood L. Wang K. Molecular cloning and characterization of prostase, an androgen-regulated serine protease with prostate-restricted expression. Proceedings of the National Academy of Sciences of the United States of America. 96(6):3114-9, 1999.

Noordzij MA. van Steenbrugge GJ. Verkaik NS. Schroder FH. van der Kwast TH. The prognostic value of CD44 isoforms in prostate cancer patients treated by radical prostatectomy. Clinical Cancer Research. 3(5):805-15, 1997.

Park M. Oncogenes. In *The Genetic Basis of Human Cancer* (Eds. Vogelstein B and Kinzler KW), pp. 205-228, McGraw-Hill Health Professions Division, 1998.

Rittenhouse HG. Finlay JA. Mikolajczyk SD. Partin AW. Human Kallikrein 2 (hK2) and prostate-specific antigen (PSA): two closely related, but distinct, kallikreins in the prostate. [Review] [457 refs] Critical Reviews in Clinical Laboratory Sciences. 35(4):275-368, 1998.

Qian J. Bostwick DG. Takahashi S. Borell TJ. Herath JF. Lieber MM. Jenkins RB. Chromosomal anomalies in prostatic intraepithelial neoplasia and carcinoma detected by fluorescence in situ hybridization. Cancer Research. 55(22):5408-14, 1995.

Saedi MS. Hill TM. Kuus-Reichel K. Kumar A. Payne J. Mikolajczyk SD. Wolfert RL. Rittenhouse HG. The precursor form of the human kallikrein 2, a kallikrein homologous to prostate-specific antigen, is present in human sera and is increased in prostate cancer and benign prostatic hyperplasia. Clinical Chemistry. 44(10):2115-9, 1998.

Saki H. Yogi Y. Minami Y. Yushita Y. Kanetake H. Saito Y. Prostate specific antigen and prostatic acid phosphatase immunoreactivity as prognostic indicators of advanced prostatic carcinoma. Journal of Urology. 149(5):1020-3, 1993.

Sakr WA. Macoska JA. Benson P. Grignon DJ. Wolman SR. Pontes JE. Crissman JD. Allelic loss in locally metastatic, multisampled prostate cancer. Cancer Research. 54(12):3273-7, 1994.

Scardino PT. Weaver R. Hudson MA. Early detection of prostate cancer. [Review] [102 refs] Human Pathology. 23(3):211-22, 1992.

Sgrignoli AR. Walsh PC. Steinberg GD. Steiner MS. Epstein JI. Prognostic factors in men with stage D1 prostate cancer: identification of patients less likely to have prolonged survival after radical prostatectomy [see comments]. Journal of Urology. 152(4):1077-81, 1994.

Shoker BS. Sloane JP. DCIS grading schemes and clinical implications. [Review] [40 refs] Histopathology. 35(5):393-400, 1999.

Silverstein MJ. Masetti R. Hypothesis and practice: are there several types of treatment for ductal carcinoma in situ of the breast?. [Review] [53 refs] Recent Results in Cancer Research. 152:105-22, 1998.

Stamey TA, McNeal JE, Yemoto CM, Sigal BM, Johnstone IM. Biological determinants of cancer progression in men with prostate cancer. JAMA 281:1395-1400, 1999.

Tsihlias J. Kapusta LR. DeBoer G. Morava-Protzner I. Zbieranowski I. Bhattacharya N. Catzavelos GC. Klotz LH. Slingerland JM. Loss of cyclin-dependent kinase inhibitor p27Kip1 is a novel prognostic factor in localized human prostate adenocarcinoma. Cancer Research. 58(3):542-8, 1998.

Ueda T. Ichikawa T. Tamaru J. Mikata A. Akakura K. Akimoto S. Imai T. Yoshie O. Shiraishi T. Yatani R. Ito H. Shimazaki J. Expression of the KAI1 protein in benign prostatic hyperplasia and prostate cancer. American Journal of Pathology. 149(5):1435-40, 1996.

Umbas R. Schalken JA. Aalders TW. Carter BS. Karthaus HF. Schaafsma HE. Debruyne FM. Isaacs WB. Expression of the cellular adhesion molecule E-cadherin is reduced or absent in high-grade prostate cancer. Cancer Research. 52(18):5104-9, 1992.

Umbas R. Isaacs WB. Bringuier PP. Schaafsma HE. Karthus HF. Oosterhof GO. Debruyne FM. Schalken JA: Decreased E-cadherin expression is associated with poor prognosis in patients with prostate cancer. Cancer Research. 54(14):3929-33, 1994.

Vallet V. Chraibi A. Gaeggeler HP. Horisberger JD. Rossier BC. An epithelial serine protease activates the amiloride-sensitive sodium channel. Nature 389(6651):607-10, 1997.

van de Vijver MJ. Ductal carcinoma in situ of the breast: histological classification and genetic alterations. [Review] [69 refs] Recent Results in Cancer Research. 152:123-34, 1998.

Yagoda A. Petrylak D. Cytotoxic chemotherapy for advanced hormone-resistant prostate cancer. [Review] [63 refs] Cancer. 71(3 Suppl):1098-109, 1993.

Yu JX. Chao L. Chao J. Prostasin is a novel human serine proteinase from seminal fluid. Purification, tissue distribution, and localization in prostate gland. Journal of Biological Chemistry. 269(29):18843-8, 1994.

Yu JX. Chao L. Chao J. Molecular cloning, tissue-specific expression, and cellular localization of human prostasin mRNA. Journal of Biological Chemistry. 270(22):13483-9, 1995.

Yu JX. Chao L. Ward DC. Chao J. Structure and chromosomal localization of the human prostasin (PRSS8) gene. Genomics. 32(3):334-40, 1996.

Zaugg K. Bodis S. Is there a role for molecular prognostic factors in the clinical management of ductal carcinoma in situ (DCIS) of the breast?. [Review] [49 refs] Radiotherapy & Oncology. 55(2):95-9, 2000.

Robert J. Bridges, Ben B. Newton, Joseph M. Pilewski, Daniel C. Devor, Christopher T. Poll, Rod L. Hall, "Na$^+$transport in normal and CF human bronchial epithelial cell is inhibited by BAY 39-9437," Am J Physiol Lung Cell Mol. Physiol, 281: pp. L16-L23 (2001).

* cited by examiner

Figure 1

SEQ ID No. 3

| G | B | X | Z | Z | Z | Z | X | X | X | X | L | I | A | R |
|---|---|---|---|---|---|---|---|---|---|---|---|---|---|---|
| $P_{15}$ | $P_{14}$ | $P_{13}$ | $P_{12}$ | $P_{11}$ | $P_{10}$ | $P_9$ | $P_8$ | $P_7$ | $P_6$ | $P_5$ | $P_4$ | $P_3$ | $P_2$ | $P_1$ |

Figure 2A

SEQ ID No. 1

| L | I | A | R |
|---|---|---|---|
| $P_4$ | $P_3$ | $P_2$ | $P_1$ |

L = Leu
I = Ile
A = Ala
R = Arg

Figure 2B

SEQ ID No. 2

| G | B | X | Z | Z | Z | Z | X | X | X | X |
|---|---|---|---|---|---|---|---|---|---|---|
| $P_{15}$ | $P_{14}$ | $P_{13}$ | $P_{12}$ | $P_{11}$ | $P_{10}$ | $P_9$ | $P_8$ | $P_7$ | $P_6$ | $P_5$ |

X = Any amino acid
Z = short chain amino acids such as Ala, Gly or Ser
B = Thr or Ser
G = Gly

4A

4B

4C

SEQUENCE LISTING

```
<160> NUMBER OF SEQ ID NOS: 8

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Leu Ile Ala Arg
  1

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Thr or Ser
<220> FEATURE:
<221> NAME/KEY: MOD_RES
<222> LOCATION: (3)
<223> OTHER INFORMATION: variable amino acid
<220> FEATURE:
<221> NAME/KEY: MOD_RES
<222> LOCATION: (4)..(7)
<223> OTHER INFORMATION: short chain amino acid such as Ala, Gly or Ser
<220> FEATURE:
<221> NAME/KEY: MOD_RES
<222> LOCATION: (8)..(11)
<223> OTHER INFORMATION: variable amino acid

<400> SEQUENCE: 2

Gly Xaa Xaa Xaa Xaa Xaa Xaa Xaa Xaa Xaa Xaa
  1               5                   10
```

```
<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Thr or Ser
<220> FEATURE:
<221> NAME/KEY: MOD_RES
<222> LOCATION: (3)
<223> OTHER INFORMATION: variable amino acid
<220> FEATURE:
<221> NAME/KEY: MOD_RES
<222> LOCATION: (4)..(7)
<223> OTHER INFORMATION: short chain amino acid such as Ala, Gly or Ser
<220> FEATURE:
<221> NAME/KEY: MOD_RES
<222> LOCATION: (8)..(11)
<223> OTHER INFORMATION: variable amino acid

<400> SEQUENCE: 3

Gly Xaa Xaa Xaa Xaa Xaa Xaa Xaa Xaa Xaa Xaa Leu Ile Ala Arg
 1               5                  10                  15

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggaattctcc cagttcaact ctctgtc                                          27

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ccgcctcgag tcagggcttg ttcacctggc                                       30

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggaattctcc cacttcaatc ctctgtc                                          27

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 7
ggaattctac gggtttgttt atctgcc                                              27

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Leu Glu Glu Leu Gly Ser Asn Thr Gly Ile Gln
  1               5                  10
```

INHIBITORS OF PROSTASIN

The present invention relates to identification of inhibitors of prostasin, and claims the benefit of priority from Provisional Patent Application 60/379,469 filed on May 10, 2002.

Funded in part by the Department of Defense Prostate Cancer Research Program Grants Number DAMD 17-98-1-8590, and DAMD 17-02-1-0032.

FIELD OF THE INVENTION

Background of the Invention

Prostasin is a serine protease known to be expressed at highest levels in the semen and prostate, however, it is also expressed in other tissues at low levels. In seminal fluid prostasin can be found in complex with a prostasin binding protein that can inhibit prostasin enzymatic activity. Prostasin mRNA is found in normal prostrate epithelial cells but is not expressed in invasive prostate cancer lines. Expression of prostasin in invasive cancer lines reduces the invasiveness of cells in vitro. Prostasin is a serine protease that may have roles in normal prostate function and in suppression of tumor cell invasion.

Prostasin expression has also been implicated in ovarian and breast cancers. It is down-regulated in invasive breast cancer cell lines.

Prostasin is also known to be an activator of the epithelial sodium channel in vitro, and is present in tissues that absorb Na+ such as the kidney, colon, lung, and salivary glands. The proper regulation of the epithelial sodium channel is crucial to maintaining sodium balance, extracellular fluid volume and blood pressure. As such, it is a protein whose regulation and expression are implicated in diseases of the kidney, hypertension, and respiratory diseases.

Prostasin may also have a role in regulating various aspects of the male reproductive system, which affect male fertility.

Prostasin's physiological functions are not well characterized, and at present, neither are its substrates, inhibitors, co-factors or other regulators. Identifying these factors would be very advantageous in the ultimate development of drug therapies, assays and diagnostic tools for diseases that relate to the regulation and function of prostasin.

Prostasin belongs to the group of proteases called "serine proteases." Serine proteases are a family of enzymes that cut peptide bonds in other proteins. This activity is dependent on a set of amino acid residues in the active site of the enzyme, one of which is always a serine.

Serine proteases are inhibited by a group of inhibitors named serpins, so called because they are serine protease inhibitors. Structurally, serpins have a central sheet and an exposed reactive center loop (RCL) at the top of the protein that contains the target cleavage sequences. Serpins work by mimicking the three-dimensional structure of a normal substrate of the protease, and the serine protease binds the serpin instead of its normal substrate. This function alone would block any further activity by the proteases. However, the proteases also cleave the serpin, forming a covalent bond linking the molecules and making a change in the three dimensional structure of the serpin which moves the attached protease to a location where it can be destroyed.

U.S. Pat. No. 6,420,157 to Darrow, et al. describes an expression vector system which identifies modulators and substrates of prostasin, but the present invention permits identification of such substances without laboratory experimentation.

SUMMARY OF THE INVENTION

One aspect of the invention relates to inhibitors of prostasin.

Another aspect of the invention relates to a method for inhibiting prostasin.

Another aspect of the invention relates to a method for identification of amino acid sequences that are the best inhibitors of prostasin.

Another aspect of the invention relates to methods for selecting compounds which are therapeutically useful for treating diseases which involve prostasin regulation.

A further aspect of the invention relates to methods for selecting compounds which are useful for regulation of male fertility.

Further objects and advantages of this invention will be apparent from the following detailed description of a presently preferred embodiment which is illustrated schematically in the accompanying drawings

BRIEF DESCRIPTION OF THE DRAWINGS

FIG. 1 shows the amino acid sequence for the "leu-ile-ala-arg (LIAR)" sequence of the invention (SEQ ID No. 3).

FIG. 2 shows the amino acid sequence for a "regular" serpin sequence (SEQ ID No 2).

Figure 3:
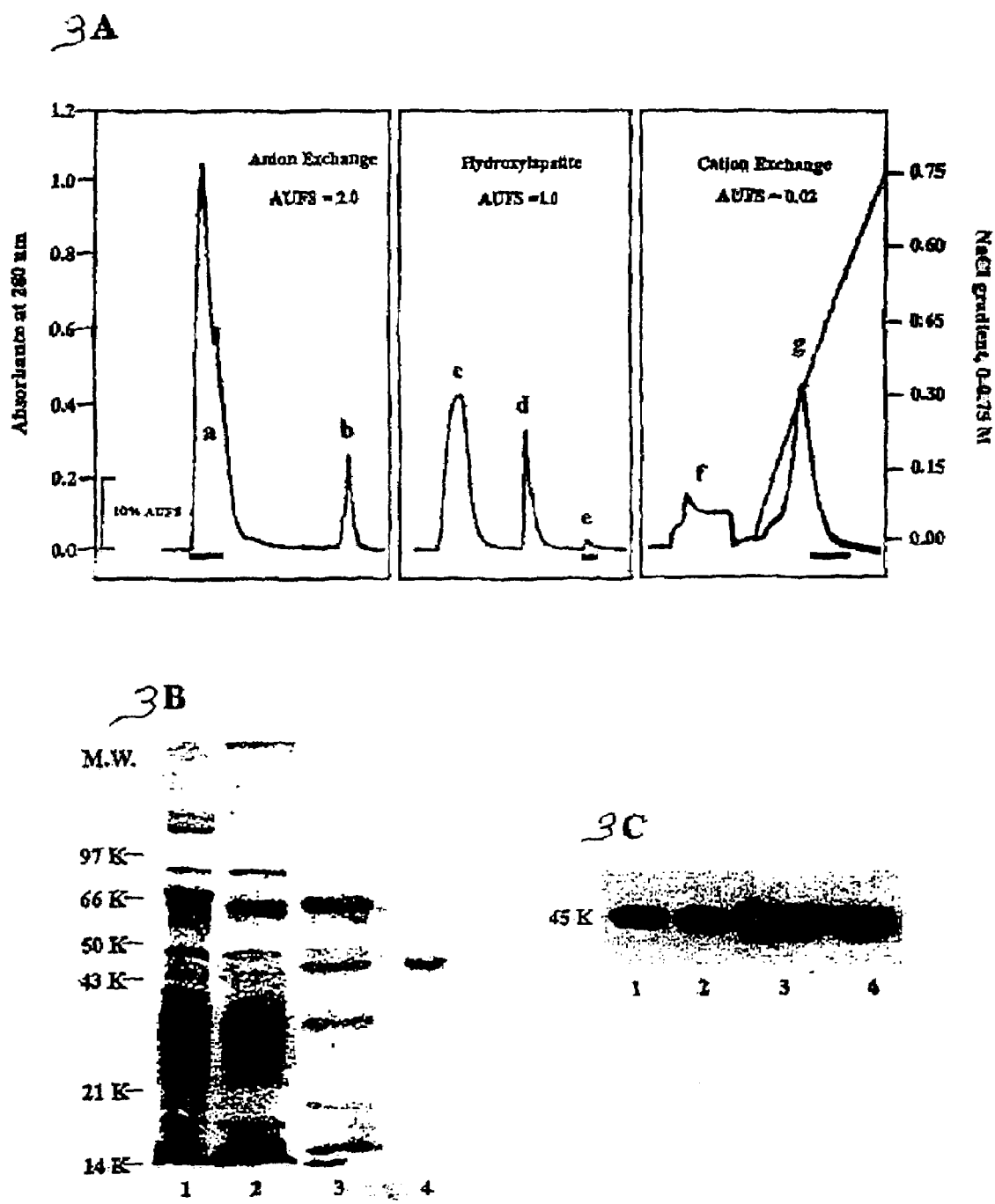
FIG. 3A shows representative purification profiles for each purification step.
FIG. 3B shows proteins from each purification step subjected to SDS-PAGE/Coomassie blue staining.
FIG. 3C shows a Western blot analysis using mPBP antibody.

Prostasin antibody recognizes purified prostasin but not purified mPBP. The mPBP antibody recognizes purified mPBP but not purified prostasin.

FIG. 4B shows the time course of complex formation between prostasin and mPBP.

FIG. 4C shows mPBP—prostasin complex formation inhibited in presence of serine protease inhibitor aprotinin (lane 3) PMSF (lane 4) or heparin (lane 5) or mPBP antibody (lane 1) lane 2 is prostasin-mPBP complex as a control.

Figure 5:
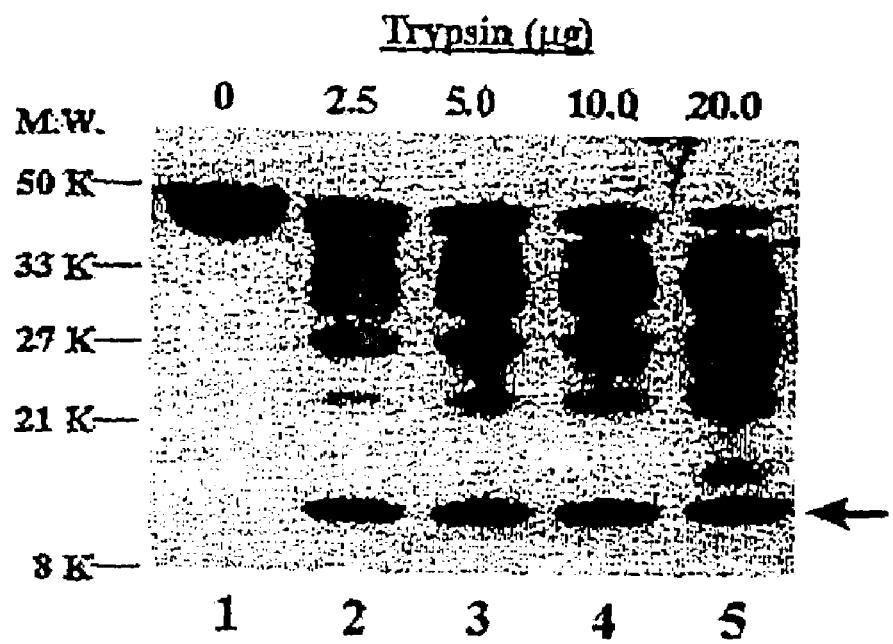

FIG. 5 shows Purified mPBP trypsin digested and separated using Tricine/SDS-PAGE, and immunodetected with mPBP antibody. Band indicated with arrow sent for sequence analysis and shown to be identical to sequences between position 26 and 37 of PN-1.

FIG. 6A shows prostasin-mPBP complex with thrombin and thrombin-mPBP formation and its pH dependence.

FIG. 6B shows Heparin at 0.25 unit/reaction abolishes complex formation between prostasin-mPBP but not between thrombin-mPBP.

Figure 7:
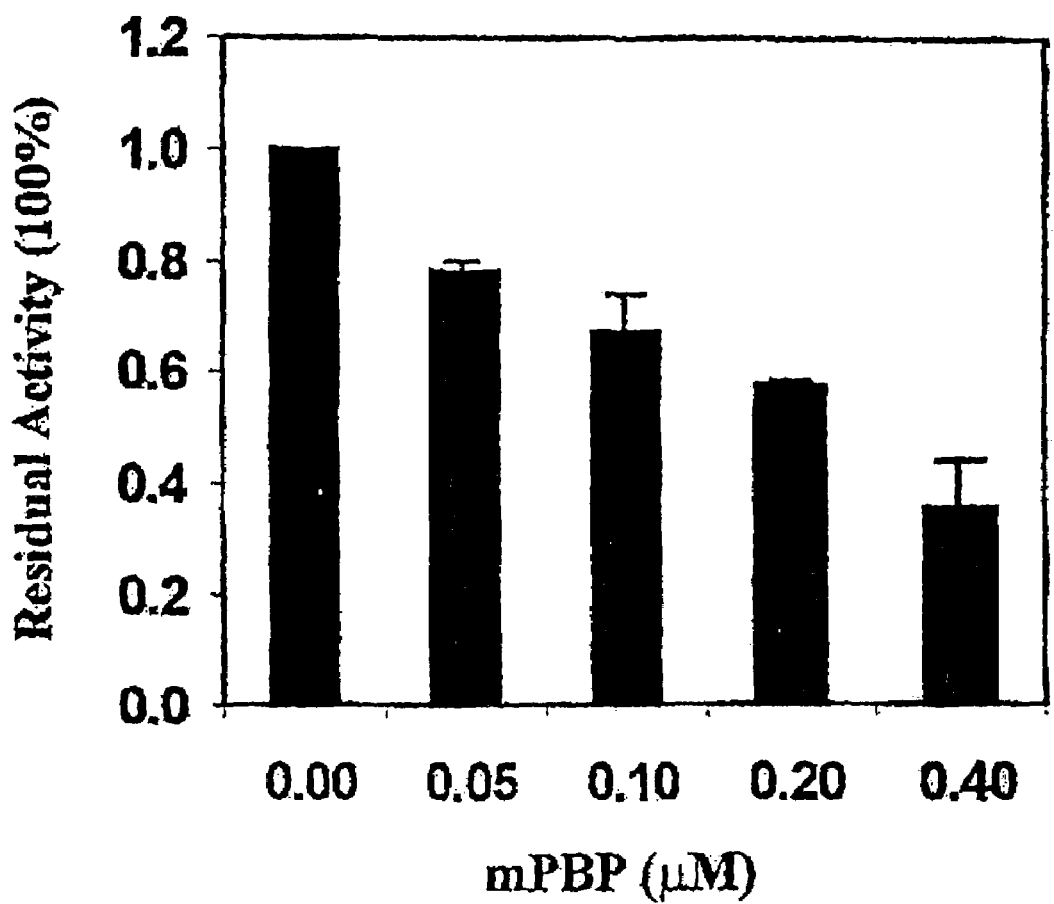

FIG. 7 shows inhibition of prostasin activity when incubated with mPBP at different concentrations.

Figure 8:
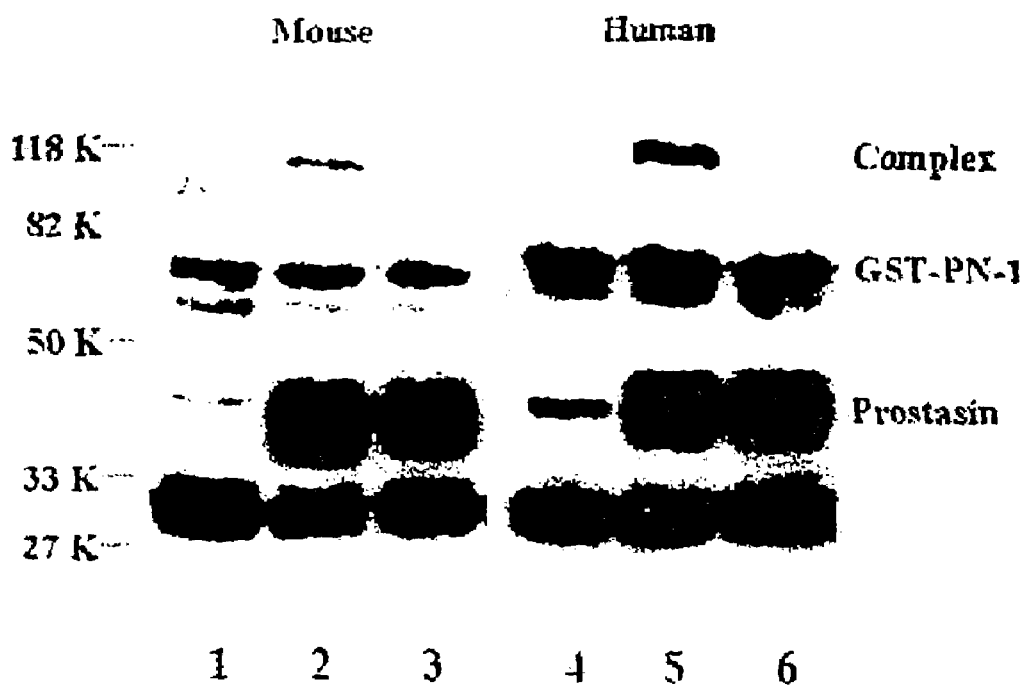

FIG. 8 shows GST-mPN-1 (lane 1) and GST-hPN-1 (lane 4) form a 100 kDa complex when incubated with prostasin (lanes 2 and 5). Complex formation is inhibited by aprotinin (lanes 3 and 6).

DETAILED DESCRIPTION OF THE INVENTION

Before explaining the disclosed embodiment of the present invention in detail it is to be understood that the invention is not limited in its application to the details of the particular arrangement shown since the invention is capable of other embodiments. Also, the terminology used herein is for the purpose of description and not of limitation.

Schecter and Berger, in their 1967 article "On the size of the active site in proteases," Biochem. Biophys. Res. Commun. 27:157162, have established nomenclature for describing the RCL of molecules that are cleaved by serine proteases, now widely used in the literature. This nomenclature designates the amino acids on each side of the scissile bond, the place where cleavage occurs, as follows:

Amino terminus . . . $P_{15}$ . . . $P_4P_3P_2P_1$ Scissile Bond $P'_1P'_2P'_3P'_4$ . . . Carboxyl terminus, wherein P or P' represents a single amino acid (of which there are 20, so each P and P' has 20 possibilities), and the subscript number below the P or P' represents the number of the amino acids from the scissile bond. (The dots indicate an interrupted amino acid sequence, for example $P_{15}$ is not directly adjacent to the amino terminus)

It is a novel finding of the present invention that the best substrates of prostasin are those molecules which have leu-ile-ala-arg (the "liar") sequence in the $P_1$-$P_4$ positions respectively, hereinafter referred to as Sequence ID 1, and shown in FIG. 1 and at the $P_5$-$P_{15}$ position do not have a sequence characteristic of serine protease inhibitors, that is, they have a random and not a "regular" serpin sequence. A "regular" serpin sequence is one in which a consensus has determined that $P_9$-$P_{12}$ are occupied by residues with short side-chains such as alanine, glycine or serine, and P14 is usually threonine or serine and $P_{15}$ is usually glycine. The regular serpin sequence is hereinafter referred to as Sequence ID 2 and shown in FIG. 2.

In classical "lock and key" theory of enzyme-substrate action, the protease is the "lock" having openings that precisely match the "key" or substrate that comes in to fit the protease. An optimally fit substrate is the best substrate and will be cleaved at the scissile bond. The fate of the protease substrate interaction is largely dependent on the types of residues at $P_5$-$P_{15}$ which determine that it is either a substrate, or an inhibitor.

Once a substrate binds to the prostasin protease via its P1-P4a cleavage will occur at the scissile bond, and residues to the right of the cleavage (i.e., P'1-P'4 and beyond will dissociate from the protease. If P5-P15 are random, then the rest of the substrate will eventually dissociate from the protease regenerating an active prostasin serine protease, ready for cleavage on the next molecule. If P5-P15 conform to the serpin class of proteins while P1-P4 are the same as the "liar" (SEQ ID NO: 1) sequences of the invention, the scissile bond will still be cleaved and the P'1-P'4 beyond will still dissociate, but the P1-P15 and the rest of the protein will be "stuck" on the prostasin protease, permanently disabling it from cleaving any more proteins.

Registries of gene sequences are available for researches and other interested parties to search through. The National Institute of Health (NIH) provides a gene sequence database called Genbank, which assigns accession numbers to gene sequences, which have been submitted to it. The present invention will permit a researcher to search for an appropriate inhibitor of prostasin by searching the Genebank for a gene sequence that would code for a protein of the indicated structure, and obtain an appropriate inhibitor for further use.

The following examples are provided for purposes of illustration and not limitation Example 1

Purification of a Prostasin-Binding Protein (mPBP)

Sample preparation—The procedure was carried out as described in Chen, L. M., Skinner, M. L, Kauffman, S. W., Chao, J. Chao, L. Thaler, C. D. and Chai, K. X., J. Biol. Chem 276, 21434-21442 (2001) (incorporated herein by reference) with modifications. Mouse seminal vesicle fluid was expressed in buffer A (20 mM sodium phosphate pH, 6.8) at a ratio of one pair of seminal vesicles per 1.0 ml of buffer. The sample was then centrifuged at 10,000×g for 30 mins at 4 degrees C. to remove insoluble material.

The following chromatography steps were performed at room temperature.

Anion-exchange chromatography—Two milliliters of the mouse seminal vesicle supernatant were applied onto an anion-exchange Econ-Cartridge (Q, 1 ml: Bio-Rad, Hercules, Calif.) equilibrated with buffer A, at a flow rate of 1 ml/min. After washing with 10 ml buffer A, the cartridge was eluted with 10 ml of 1M NaCl/buffer A. Prostasin-binding activity was monitored by means of a prostasin-binding assay as described in Chen et al (2001), Hydroxylapatite chromatography—Fractions containing the prostasin-binding activity from the Q cartridge were applied onto a hydroxylapatite Econ-Cartridge (http, 1 ml; Bio-Rad) equilibrated with buffer A. The cartridge was washed with buffer A (10 ml) and eluted with 0.2 M sodium phosphate buffer (pH 6.8, 10 ml) followed by 0.5 M sodium phosphate buffer (pH 6.8, 10 ml).

Cation-exchange chromatography—Factions containing the prostasin-binding activity from the http cartridge were diluted with buffer A and applied onto a cation-exchange Econ-Cartridge were diluted with buffer A and applied onto a cation-exchange Econ-Cartridge (CM, 1 ml; Bio-Rad) equilibrated with buffer A. After washing with buffer A, the cartridge was eluted with a 0±0.75 linear NaCl gradient in buffer A (20 ml). Fractions containing prostasin-binding activity were collected and concentrated through a Centricon-10 concentrator (Millipore, Bedford, Mass.) with several changes of PBS (phosphate-buffered saline, pH 7.4, Life Technologies, Gaithersburg, Md.) and then stored at −20 degrees C. before further characterization.

Scaled-up purification was performed as described above, except that the first anion-exchange chromatography was performed using the DEAD CL-6B agarose (2.5×20 cm, Amersham Pharmacia Biotech, Piscataway, N.J.). The subsequent purification steps were carried out by using 5-ml cartridges (Bio-Rad)

The presence of mouse prostasin-binding protein (mPBP) in each purification step was monitored using a prostasin-binding assay as described in example 2 below. FIG. 3A shows the representative purification profiles for each step. Two milliliters of mouse seminal vesicle fluid were applied onto the Q cartridge and eluted with 1 M NaCl/buffer A. Fractions were subjected to the prostasin binding assay followed by western blotting using a prostasin antibody. The mPBP was present in flow-through fractions (peak a, indicated by the horizontal solid bar) but not the 1M naCl eluent (peak b). The mPBP-containing fractions were pooled and applied onto the http cartridge. After washing with buffer A, the cartridge was first eluted with 0.2M sodium phosphate buffer at pH 6.8 (to result in peak d) and then eluted with 0.5M sodium phosphate buffer at pH 6.8 (to result in peak e) Neither peak c (the flow-through) nor peak d contained any detectable amount of mPBP. The mPBP was detected in peak e (indicated by the horizontal solid bar). Fractions corresponding to peak e were pooled and further separated by using a CM cartridge. The CM cartridge was eluted with a linear NaCl gradient from 0 to 0.75M in buffer A. The mPBP was eluted at 0.2-0.55 NaCl buffer A (peak g, as indicated by the horizontal solid bar). The flow through fractions (peak f) did not contain mPBP. The purified mPBP was used to generate a polyclonal antibody using rabbit as the host. (see example 2 below) Proteins from each purification step were subjected to SDS PAGE/Coomassie blue staining (FIG. 3B) or western blot analysis using the mPBP antibody (FIG. 3C) As shown in FIG. 3B, the purified mPBP (lane 4,5 micrograms) migrated at '45 kDa in an SDS-PAGE under reducing conditions. As shown in FIG. 3C, the mPBP antibody recognized a 45 kDa protein in mouse seminal vesicle fluid, as well as the purified mPBP itself.

Example 2

Identification of mPBP as Protein Nexin-1

Preparation of Polyclonal Antiserum

An anti-serum against PBP was prepared according to the procedure described in Chen et al. Briefly, 0.5 ml of the purified mPBP (250 micrograms) was emulsified with an equal volume of complete Freund's adjuvant (Sigma-Aldrich, St. Louis, Mo.) and injected subcutaneously into a 1.5 kg New Zealand White female rabbit (Charles River Laboratories, Wilmington, Mass.). Booster injections were made with 100 micrograms of mPBP (emulsified with incomplete Freund's adjuvant, Sigma-Aldrich) for 3 times at 3-week intervals. Pre-immune rabbit serum was collected before the initial immunization.

Prostasin-Binding Assay and Western Blot Analysis

The procedures were performed according to Chen et al. Briefly, purified recombinant prostasin was incubated with samples from each purification step or the final purified mPBP at 37 degrees C. for 1 hour or for various times as indicated. The binding reaction was stopped by the addition of SDS sample buffer (1×SDS sample buffer=62.5 mM Tris-Hcl at Ph 6.8, 2% (v/v) glycerol, 2% SDS (w/v) and 2% Beta-mercaptoethanol). The reaction mixtures were then boiled for 5 min, and resolved in 10% SDS-polyacrylamide gels. The resolved proteins were then transferred to nitrocellulose membranes, and analyzed with either a prostasin antibody or the mPBP antibody. Signals were detected using an ECL detection procedure with the WestPico reagents (Pierce, Rockford, Ill.) following the manufacturer's protocol. The membrane was then exposed to X-ray film (Midwest Scientific, St. Louis, Mo.) The prostasin antibody was used at 1:2,000 dilution, the mPBP antibody was used at 1:10,000 dilution, and the secondary antibody (goat anti-rabbit IgG, Sigma-Aldrich) was used at 1:10,000 dilution. All antibodies were diluted in 5% non-fat milk in TBS-T (TBS-T=20 mM Tris-Hcl at pH 7.6, 0.14M NaCl and 0.1% Tween-20).

Amino Acid Sequence Analysis

The purified mPBP (6 micrograms) was incubated with various amounts of trypsin (LifeTechnologies) at 37 degrees C. for 30 minutes, and subjected to Tricine/SDS-PAGE (Schagger, H., and von Jagow, G. (1987) Anal. Biochem. 166, 368-379.) followed by transferring to the Immobilon-P membrane (Fisher, Pittsburgh, Pa.). One membrane was subjected to immunodetection with the mPBP antibody, an identical membrane was stained with 0.02% Coomassie blue R-250 in 40% methanol and 5% acetic acid for 30 seconds. The membrane was then destained in 40% methanol and 5% acetic acid for 1 min, rinsed in distilled water for 3×5 min to remove the destaining solution, and air dried. A stained band at ~10 kDa, which was recognized by the mPBP antibody, was for amino acid sequence analysis at the Protein Core Facility of the University of Florida (Gainesville, Fla.)

Enzymatic Assay

Recombinant human prostasin was purified as described in Chen et al. A synthetic substrate, N-t-Boc-Gln-Ala-Arg-7-amido-4-methyl coumarin (QAR-AMC) was purchased from Sigma-Aldrich. The purified mPBP (concentration range 0-0.4 micromolar) was incubated with prostasin (0.8 micromolar) for 30 mins at 37 degrees C. The binding reaction mixture (20 microliters) was then added to 80 microliters of 50 micromolar Tris-HCL) pH 8.0/0.1% bovine serum albumin containing the QAR-AMC substrate (final concentration: 100 micromolar) in 96-well microtiter plates (Costar 3903, Cambridge, Mass.). The velocity of substrate hydrolysis was measured using a Wallac 1420 Victor mulitlabel counter at wavelength 355 nm and wavelength 460 nm. The residual activity of prostasin (velocity of the inhibited enzyme reaction/velocity of the uninhibited enzyme reaction) as plotted versus the mPBP concentration.

Molecular Cloning, Expression, and Purification of Recombinant Mouse and Human Protease Nexin-1 (PN-1, Spi-4)

A cDNA encoding the mature peptide of mouse protease nexin-1 (PN-1 or Spi-4) was cloned from mouse seminal vesicle mRNA by reverse-transcription-polymerase chain reaction (RT-PCR). Total RNA of mouse seminal vesicle was isolated using a procedure described in Chirgwin, J. M., Przybyla, A. E., MacDonald, R. J. and Rutter, W. J. (1979) Biochemistry 18:5294-5299 (incorporated herein by reference.), an Oligotex mRNA Mini Kit from QIAGEN (Valencia, Calif.) was used to isolate the mRNA. The following oligonucleotide primers were used in the RT-PCR to generate the mouse PN-1cDNA: upstream: 5'GGAATTC TCC CAG TTC AAC TCT CTG TC-3' (SEQ ID NO: 4) and downstream: 5'-CCGCCTCGAG TCA GGG CTT GTT CAC CTG GC-3' (SEQ ID NO: 5). The underlined sequences are adapters for restriction enzyme sites. The mouse PN-1 specific sequences were derived from the Genbank™ mouse PN-1 sequence of X70296. The upstream primer sequence corresponds to base numbers 206-225 of X70296, the first codon (206-208) is that of Ser, the amino-terminal residue of the mature mouse PN-1 peptide (Vassalli, 1993) The downstream primer sequence corresponds to base numbers 1,323-1,342 including the termination Odon (1,340-1,342). The RT-PCR was performed as described in Chen, L. M., Hodge, G. B., Guarda, L. A., Welch, J. L., Greenberg, N. M. and Chai, K. X. (2001), and incorporated herein by reference using 3 micrograms of mouse seminal vesicle mRNA as the template. A single cDNA band was amplified. The Taq DNA polymerase was removed by phenol/chloroform extraction, and the cDNA was treated with EcoR I and Xho I under proper buffer conditions. The restriction-modified cDNA was then inserted into the p'GEX-6P-1 vextor (Amersham Pharmacia Biotech) at the corresponding sites, resulting in a fusion gene construct that encodes GST-mPN-1 (GST: glutathione-5-transferase) The amplified PN-1 portion of the fusion gene was completely sequenced, no error in the PN-1 sequence was found. A human PN-1 c-DNA encoding the mature peptide was cloned from the total RNA of the human breast carcinoma cell line MDA-MB-435s (American Type Culture Collection, Manassa, Va. essentially as described above, resulting in the GST-hPN-1 construct. The printers used for the cloning wee: upstream: 5'GGAATTC TCC CAC TTC AAT CCT CTG TC-3' (SEQ ID NO: 6), downstream: 5'GGAATTC TAC GGG TTT GTT TAT CTG CC-3'/(SEQ ID NO: 7). The underlined sequences are adapters for restriction enzyme sites. The human PN-1 specific sequences were derived from the GenBank™ human PN-1 sequence of A03911. The upstream primer sequence corresponds to base numbers 82-101 of A03911, the first codon (82-84) is that of Ser, the amino terminal residue of the mature human PN-1 peptide. (Scott, R W., Bergman, B. L., Bajpai, A, A. Hersh, R. T, Rodriguez., H., Jones, B. N. Barreda, C., Watts, S, and Baker, J. B. (1985) J. Biol Chem 260:7029-7034). The downstream primer sequence corresponds to base numbers 1,199-1,218, including the termination codon (1,216-1,218). The GST-mPN-1 and the GST-hPN-1 constructs were then transformed into the TOPP-10 strain of E. coli cells (Stratagene, LaJolla, Calif.) For production of the recombinant fusion proteins, cells harboring the constructs were frown to an optical density of 0.8 (at 600-nm wavelength) and recombinant protein expression was induced with 0.2 mM of IPTG (isopropylthio-beta-galactoside) at 37 degrees with shaking at 250 rpm for 1 h. Cells were collected by centrifugation at 4000 rpm for 20 minutes at 4 degrees C. washed in 1×PBS (pH 7.4) and re-centrifuged with the same settings. GST-mPN-1 or GST-gPN-1 was then purified by glutathione-agarose affinity chromatography using protocols recommended by the manufacturer (Amersham Pharmacia Biotech).

Figure 4:
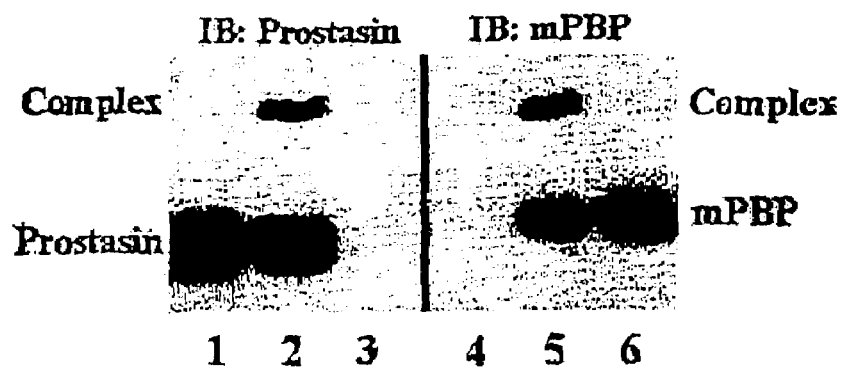
FIG. 4A shows a Western blot analysis using mPBP antibody and a prostasin antibody and both antibodies recognize prostasin-mPBP complex at 82 kDa.
Figure 4:
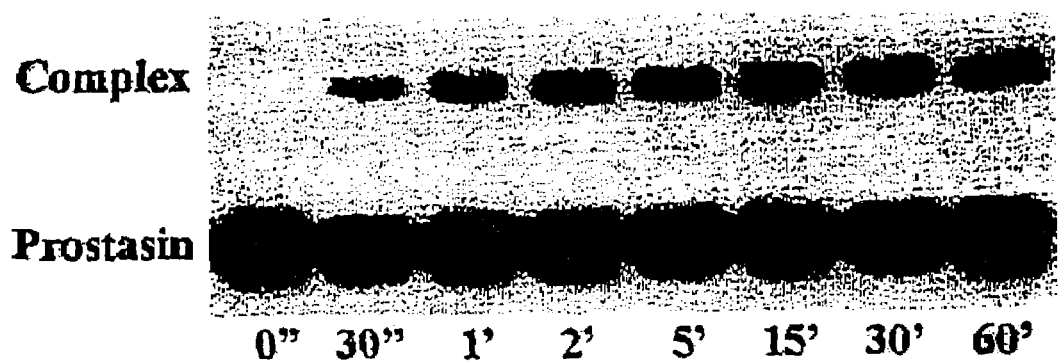
Figure 4:
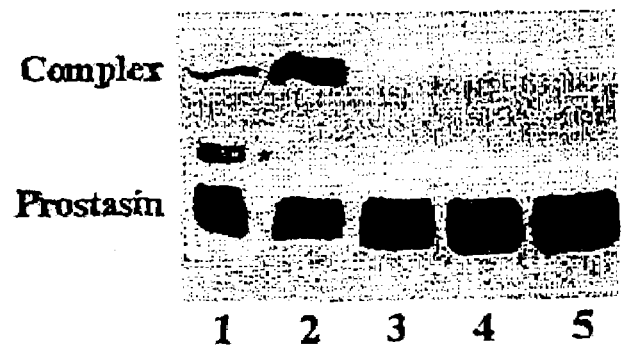

The purified mPBP was tested for its biochemical activities using the prostasin binding assay. Complex formation between mPBP and purified prostasin was analyzed by western blotting using the mPBP antibody and a prostasin antibody. Both antibodies recognized the complex of prostasin-mPBP at 82 kDa (FIG. 4A, lanes 2 and 5) The prostasin antibody also recognized the purified prostasin (FIG. 4A, lane 1) unbound prostasin (FIG. 4A, lane 2) but not the purified prostasin (FIG. 4, lane 6) unbound mPBP, but not the purified prostasin (FIG. 4, lane 4) FIG. 4B shows the time-course of complex formation between prostasin and mPBP. The complex was detected after 30 seconds of incubation and progressed during the incubation time course (60 minutes). As shown in FIG. 4C, the complex formation was inhibited in the presence of the serine protease inhibitor aprotinin (lane 3) or PMSF (lane 4) or heparin (lane 5) or the mPBP antibody (lane 1). The complex formation of prostasin and mPBP was used as a control (FIG. 4C, lane 2).

To reveal the identity of mPBP the purified mPBP was subjected to a trypsin digestion and the digested mixture was separated using Tricine/SDS-PAGE. After transferring the resolved samples to the Immobilon-P membrane, one set of the samples was immunodetected with the mPBP antibody. In the sample without trypsin digestion (FIG. 5, lane 1) the mPBP antibody recognized a single band at 45 kDa. With increasing amounts of trypsin added in the digestion mixture, several mPBP immunoreactive bands wee detected (FIG. 5, lanes 2-5) In particular, a 10 kDa band (indicted by an arrow) was separated furthest in the gel from other bands. The corresponding band in a set of the exact samples transferred to an Immobilon-P membrane, stained with Coomassie blue, was sent for amino acid sequence analysis. The amino-terminal sequence of this fragment was determined to be SLEELG-SNTGIQ (SEQ ID NO: 8), which is identical to the sequences between position 26 and 37 of the GenBank mouse protease nexin-1 (PN-1) translated sequence (accession number X70196). This result suggests that PBP may be identical to PN-1, a serine protease inhibitor (serpin).

Prostasin Binding Protein Inhibits Prostasin's Activity

The prostasin-binding protein that was identified in the seminal vesicle inhibits prostasin's activity as determined by membrane-overlay zymography. QAR-AMC was used as a substrate for prostasin to test the inhibitory activity of the purified mPBP. Prostasin (0.8 micromolar) was incubated with 0, 0.05, 0.1, 0.2 or 0.4 micromolar mPBP at 37 degrees C. for 30 mins. The reaction mixture was then to the assay buffer containing a final concentration of 100 micromolar QAR-AMC substrate. As shown in FIG. 7, when incubated with mPBP at different concentrations, prostasin's activity was inhibited in a dose dependent manner.

Prostasin Forms a Complex with Recombinant protease Nexin-1

To establish if mPBP is indeed protease nexin-1, mouse and human protease nexin-1 (PN-1) cDNA were cloned into the pGEX-6P-1 expression vector. The recombinant protein products have the schistosomal glutathione-5-transferase (GST) fused to the N-terminus of the PN-1. The GST fusion proteins were affinity-purified using glutathione-conjugated agarose-beads. For each type of recombinant protein, cleared supernatant of cell lysate from one liter of culture was incubated with 1 ml of 505 glutathione-beads. The beads were eluted with 1 ml of fresh 10 mM glutathione in 50 mM Tris-Hcl, pH 8.0. Twenty microliters of the eluent were incubated with 0.5 micrograms of recombinant prostasin at 37 degrees C. for 60 minutes in the absence or presence of aprotinin. Both the GST-mPN-1 (FIG. 8, lane 1 alone at 64 kDa) and the GST-hPN-1 (FIG. 8, lanes 2 and 5). The complex formation was inhibited by the serine protease inhibitor aprontinin (FIG. 8, lanes 3 and 6) These results further indicate that the mPBP is the serpin protease nexin-1. for this immunoblot, both the prostasin antibody and the mPBP antibody were used as the primary antibody, and a goat anti-rabbit IgG conjugated with HRP was used as a secondary antibody. An immunoreactive band at 30 kDa and two other minor immunoreactive bands at 42 kDa and 60 kDa were likely the products of non-specific degradation of the recombinant PN-1, since no protease inhibitors were added in the cell lysate during purification.

Example 3

Identification of the reactive sequence of the serpin PN-1

The reactive site sequences of PN-1 at locations $P_1$-$P_4$ are known to be Leu-ile-Ala-Arg. It has been shown with the serpin Kallistatin that its reactive site sequence was also the best for a substrate.

Example 4

Heparin and Thrombin Binding to Pn-1

It has been known that PN-1 can form complexes with various serine proteases, including thrombin. FIG. 6A shows the complex formation between prostasin-mPBP and that between thrombin-mPBP. We also tested if the complex is pH dependent because prostasins's optimum pH is 9.0. The results showed that the purified mPBP formed a complex with prostasin as well as thrombin. The complex formation of mPBP and prostasin is increased with higher pH in the binding conditions while the complex formation of mPBP and thrombin is somewhat decreased with increasing pH. We further tested if heparin may have a different effect on the complex formation between prostasin-mPBP versus on that between thrombin-mPBP. In FIG. 6B, its is shown that heparin, at 0.25 unit/reaction, completely abolished the complex formation between prostasin—mPBP but not between thrombin-PMP.

Figure 6:
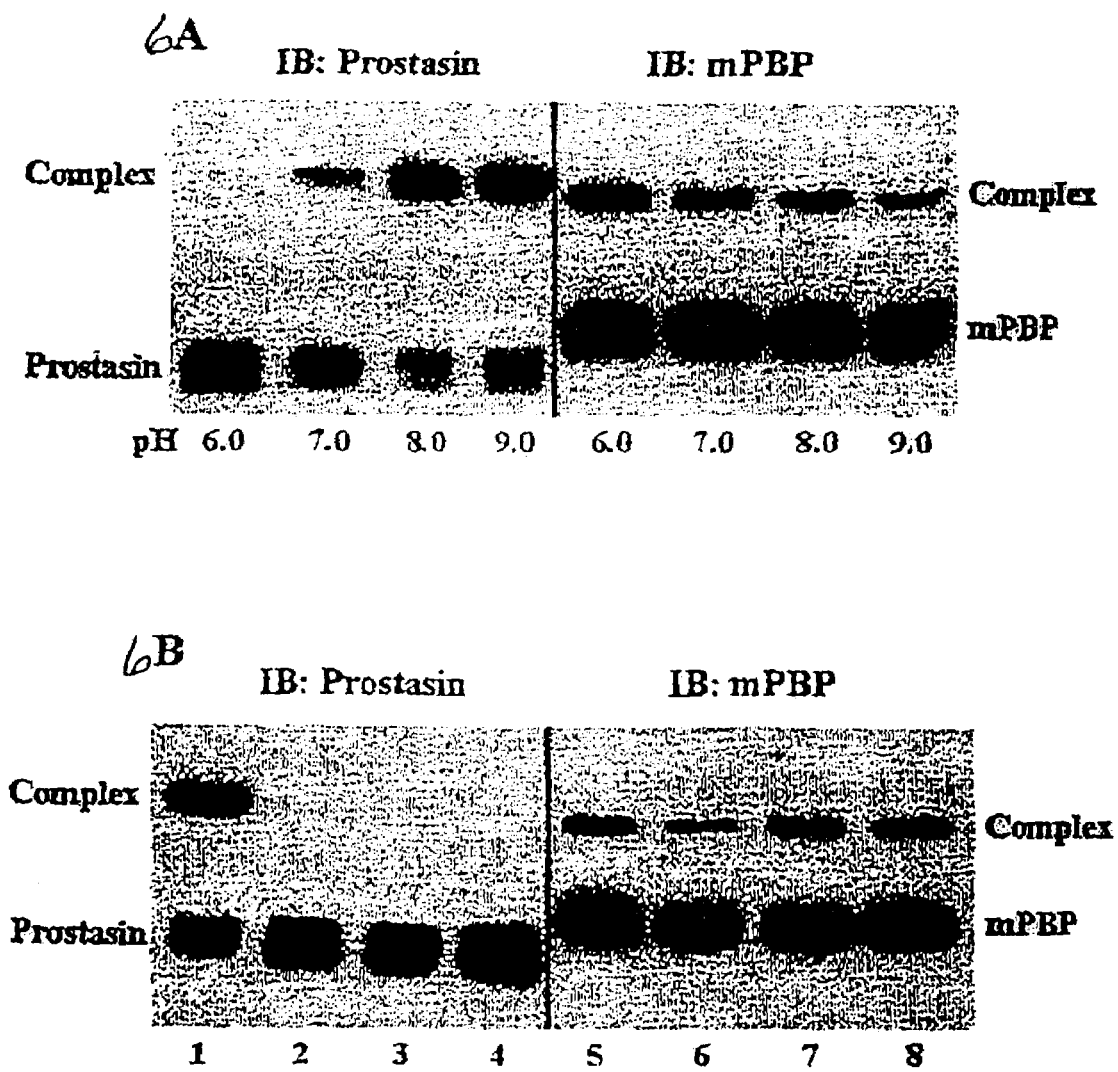

A heparin binding site has been mapped in PN-1 by Stone, S. R. Brown-Luedi, M. L., Rovelli, G. Guidolin, A. McGlynn, E. and Monard, D. (1994) Biochemistry 33:7731-7735. In the presence of heparin, the inhibitory activity of PN-1 to several serine proteases, such as thrombin and factor Xa is known to be enhanced. In the presence of heparin, however the binding between prostasin and PN-1 is abolished. Also, in an enzymatic assay using the QAR-AMC substrate, pre-incubation of mPBP and heparin was able to prevent prostasin inhibition by mPBP. This is a novel finding of PN-1's serine protease inhibition mechanism, having potentially profound implications, especially in cancer biology. PN-1 can bind to heparin-like molecules, or heparan sulfate proteoglycans (HSPG) on the cell surface and this binding apparently accelerates thrombin inhibition by PN-1. The HSPG, as a component of the extracellular matrix (ECM) is suggested to play a major role in cell-matrix signaling. Since prostasin is a GPI-anchored membrane protease which has an anti-invasive activity in vitro, it is likely that prostasin's anti-invasion activity is regulated by PN-1 and the ECM in the tissue microenvironment. Both the membrane bound and secreted prostasin may be a proteolytic regulator of cell surface events but may also serve as a receptor or a ligand in ECM signaling or tissue remodeling under physiological or pathological conditions. The complex formation between PN-1 with two of its target enzymes, prostasin and thrombin, is affected by pH (FIG. 6). Changes in intracellular pH have been shown to be a mechanism of cell signaling.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A method of inhibiting prostasin, the method comprising administering to a subject in need thereof a serine protease inhibitor having a reactive center loop consisting of a peptide of the formula $P_{15}P_{14}P_{13}P_{12}P_{11}P_{10}P_9P_8P_7P_6P_5P_4P_3P_2P_1$ wherein $P_1$ to $P_{15}$ are amino acid residues, wherein the tetrapeptide subsequence $P_4$-$P_1$ consists of SEQ ID NO:1, and wherein the subsequence $P_{15}P_{14}P_{13}P_{12}P_{11}P_{10}P_9P_8P_7P_6P_5$ consists of SEQ ID NO:2.

2. The method of claim 1, wherein the serine protease inhibitor consists of protease nexin-1 (PN-1).

3. A method of inhibiting prostasin, the method comprising contacting the prostasin with protease nexin-1 (PN-1).

4. A method for inhibiting prostasin, the method comprising administering to a subject in need thereof a serine protease inhibitor, wherein said serine protease inhibitor has a reactive center loop comprising SEQ ID NO:3.

* * * * *